(12) United States Patent
Donskoy et al.

(10) Patent No.: US 7,073,384 B1
(45) Date of Patent: Jul. 11, 2006

(54) METHOD AND APPARATUS FOR REMOTE MEASUREMENT OF VIBRATION AND PROPERTIES OF OBJECTS

(75) Inventors: Dimitri Donskoy, Hoboken, NJ (US); Nikolay Sedunov, Hoboken, NJ (US); Edward A. Whittaker, Hoboken, NJ (US)

(73) Assignee: Stevens Institute of Technology, Hoboken, NJ (US)

( * ) Notice: Subject to any disclaimer, the term of this patent is extended or adjusted under 35 U.S.C. 154(b) by 0 days.

(21) Appl. No.: 10/069,696
(22) PCT Filed: Aug. 23, 2000
(86) PCT No.: PCT/US00/23057

§ 371 (c)(1),
(2), (4) Date: Jun. 13, 2002

(87) PCT Pub. No.: WO01/14825

PCT Pub. Date: Mar. 1, 2001

Related U.S. Application Data

(60) Provisional application No. 60/150,224, filed on Aug. 23, 1999.

(51) Int. Cl.
*G01N 29/36* (2006.01)

(52) U.S. Cl. .................. 73/657; 73/655; 356/5.11
(58) Field of Classification Search .................. 73/657, 73/655, 579, 646, 627, 602, 599, 596, 1.82; 356/358, 345, 357, 432, 5.1, 5.11; 702/39, 702/40, 128, 901; 367/87

See application file for complete search history.

(56) References Cited

U.S. PATENT DOCUMENTS

| | | | | |
|---|---|---|---|---|
| 4,481,825 A | | 11/1984 | Kljuev et al. .................. 73/655 |
| 4,554,836 A | | 11/1985 | Rudd ............................ 73/657 |
| 4,755,051 A | * | 7/1988 | Cahill et al. ................. 356/460 |
| 4,768,381 A | | 9/1988 | Sugimoto ..................... 73/657 |
| 5,495,767 A | | 3/1996 | Wang et al. .................. 73/657 |
| 5,585,921 A | * | 12/1996 | Pepper et al. ............... 356/487 |
| 5,838,439 A | * | 11/1998 | Zang et al. .................. 356/484 |
| 5,883,715 A | * | 3/1999 | Steinlechner et al. ....... 356/487 |
| 5,897,494 A | | 4/1999 | Flock et al. ................. 600/407 |
| 5,915,050 A | * | 6/1999 | Russell et al. ................. 385/7 |
| 5,946,097 A | * | 8/1999 | Sanders et al. ............. 356/464 |
| 5,974,881 A | | 11/1999 | Donskoy et al. ............. 73/579 |
| 6,067,013 A | * | 5/2000 | Pejic ....................... 340/539.1 |
| 6,209,396 B1 | * | 4/2001 | Wortge et al. ................ 73/657 |

(Continued)

FOREIGN PATENT DOCUMENTS

JP          410200478 A   *   7/1998

*Primary Examiner*—Hezron Williams
*Assistant Examiner*—Jacques Saint-Surin
(74) *Attorney, Agent, or Firm*—McCarter & English, LLP

(57) ABSTRACT

A method and apparatus (10) is provided which employs phase or amplitude modulated electromagnetic probing waves (20) (in optical or microwave frequency ranges or both) emitted toward a vibrating object (8). The optical and/or microwave probing signals (20) remotely irradiate an object (8) of interest. The object (8) reflects and/or scatters the probing wave (20) toward a receiver (22). The reflected/scattered modulated signal (24) is received with a remote sensor (receiver) (22). Vibration causes additional phase modulation to the probing wave (20). At the receiving end, the signal is demodulated to extract and analyze the vibration waveform (26,28). The present invention can be utilized for nondestructive testing, monitoring of technological processes, structural integrity, noise and vibration control, mine detection, etc.

46 Claims, 4 Drawing Sheets

U.S. PATENT DOCUMENTS

| | | |
|---|---|---|
| 6,246,638 B1 * | 6/2001 | Zook et al. .................. 367/140 |
| 6,301,967 B1 | 10/2001 | Donskoy et al. .............. 73/579 |
| 6,415,666 B1 * | 7/2002 | Donskoy et al. .............. 73/627 |
| 6,505,130 B1 * | 1/2003 | Springer et al. .............. 702/40 |
| 6,545,762 B1 * | 4/2003 | Lewis et al. ................. 356/502 |
| 6,591,124 B1 * | 7/2003 | Sherman et al. ............ 600/345 |
| 2003/0074145 A1 * | 4/2003 | Springer et al. |

* cited by examiner

METHOD AND APPARATUS FOR REMOTE MEASUREMENT OF VIBRATION AND PROPERTIES OF OBJECTS This application claims the benefit of provisional application 60/150,224 filed Aug. 23, 1999.

BACKGROUND OF THE INVENTION

1. Field of the Invention

The present invention generally relates to a method and apparatus for nondestructive testing, monitoring of technological processes, determining structural integrity, noise and vibration control, and mine detection. More specifically, the present invention relates to a phase-amplitude modulated electromagnetic wave (PAM-EW) vibrometer.

2. Related Art

Existing remote vibrometers are generally based on coherent laser generated signals. These devices, known as laser-doppler vibrometers, require precision and expensive optical elements (acousto-optic modulators, gas lasers, mirrors, beam splitters, etc.) A very precise, very coherent source is required, i.e. very stable phase characteristics. Fine adjustments are necessary to achieve a desirable effect. As a result, the laser-doppler vibrometers are quite expensive and delicate instruments are best suited for laboratory use.

Another serious drawback of the conventional remote sensing devices is their high sensitivity to unwanted vibration of the transmitting/receiving assembly (TRA). In fact, vibrometers measure only relative velocity/displacement between the vibrating object and the TRA. Since the sensitivity of the conventional laser-doppler vibrometers is very high it is very difficult to isolate the TRA from such small vibrations especially under field conditions. In addition to this, conventional vibrometers are susceptible to so-called cosine error. That is, if the incident electromagnetic wave is not precisely perpendicular to the irradiated surface, an error proportional to the cosine of the angle between the line of radiation and a normal to the surface is introduced.

Efforts of others in this area include U.S. Pat. No. 5,883,715, to Steinlechner, et al., entitled Laser Vibrometer for Vibration Measurements; U.S. Pat. No. 5,897,494, to Flock, et al., entitled Vibrometer; U.S. Pat. No. 5,495,767, to Wang, et al., entitled Laser Vibrometer; and U.S. Pat. No. 4,768,381, to Sugimoto, entitled Optical Vibrometer.

None of these efforts of others teaches or suggests all of the elements of the present invention, nor do they disclose all of the advantages of the present invention.

OBJECTS AND SUMMARY OF THE INVENTION

It is a primary object of the present invention to provide a phase-amplitude modulated electromagnetic wave (PAM-EW) vibrometer.

It is an additional object of the present invention to provide a method and apparatus for measuring vibration of a vibrating object which uses a modulated electromagnetic probing wave, wherein the vibration of the vibrating object additionally modulates the modulated probing wave.

It is another object of the present invention to provide a vibrometer which uses an optical source which is not necessarily coherent, for example, an LED source.

It is even an additional object of the present invention to provide an additional set of acoustic transmitters/receivers attached directly to the electromagnetic wave transducer assembly to enhance performance.

These and other objects of the present invention are achieved by a method and apparatus which employs phase or amplitude modulated electromagnetic probing waves (in optical or microwave frequency ranges or both) emitted toward a vibrating object. The optical and/or microwave probing signals remotely irradiate an object of interest. The object reflects and/or scatters the probing wave toward to a receiver. The reflected/scattered modulated signal is received with a remote sensor (receiver). Vibration causes additional phase modulation to the probing wave. At the receiving end, the signal is demodulated to extract and analyze vibration waveform. The invention also employs an innovative method and algorithm for enhanced performance of the vibrometer by using an additional set of acoustic transmitters/receivers attached directly to the electromagnetic wave transducer assembly. This additional set and corresponding data processing algorithm allow for compensation of the unwanted background (or coupled) vibration of the vibrometer and for calibrated measurements of the displacement of the vibrating object irradiated under an arbitrary angle. The method and apparatus of the present invention can be utilized for nondestructive testing, monitoring of technological processes, structural integrity, noise and vibration control, mine detection, etc.

The present invention can be used in connection with existing methods and apparatuses for detecting land mines and detecting defects in structures. Such existing methods and apparatuses include U.S. Pat. No. 5,974,881, dated Nov. 2, 1999 to Donskoy, et al. and pending U.S. application Ser. No. 09/239,133, filed Jan. 28, 1999 by Donskoy, et al., the entire disclosures of which are expressly incorporated herein by reference.

BRIEF DESCRIPTION OF THE DRAWINGS

Other important objects and features of the present invention will be apparent from the following Detailed Description of the Invention taken in connection with the accompanying drawings in which:

FIG. 3b is a graph of the results of the experiment shown in FIG. 3a.

DETAILED DESCRIPTION OF THE INVENTION

Figure 1:
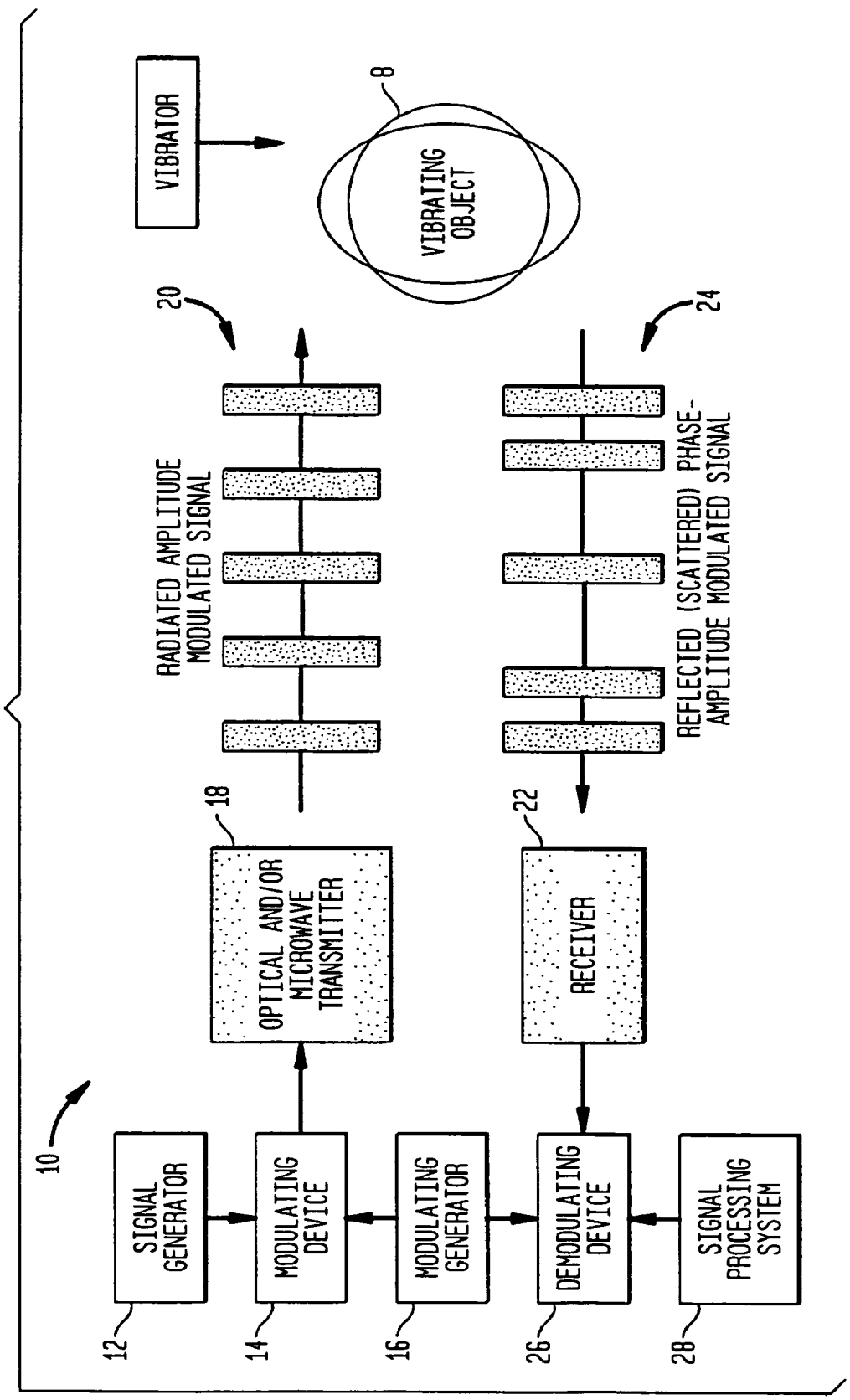
FIG. 1 is a schematic view of the method and apparatus of the present invention.

The present invention relates to a method and apparatus which employs phase or amplitude modulated electromagnetic probing waves (in optical or microwave frequency ranges) emitted toward a vibrating object. This is shown schematically in FIG. 1. The apparatus is generally indicated at 10. A signal is generated by the signal generator 12, and then modulated by the modulating device 14 which receives a modulating signal from the modulating generator 16. Preferably, the signal is amplitude modulated. The optical or microwave probing signals 20 are transmitted by transmitter 18 and remotely irradiate an object 8 of interest. The object 8 reflects and/or scatters the probing wave 20 toward to a receiver 22, where it is received. Vibration of object 8 causes additional phase modulation to the probing wave 20, based on the fact that object 8 is vibrating, which becomes amplitude/phase modulated signal 24. At the receiving end, the signal 24 is demodulated by demodulation device 26, according to signal processing system 28, to extract and analyze vibration waveform.

The present invention can be used regardless of coherency of the emitting radiation, thus eliminating need in precision and expensive optical elements. A laser, or even a light emitting diode (LED) can be used as the source. The intensity is modulated at a very high frequency, for example in the GHz range. This results in significant cost reduction of the vibrometer.

The use of microwave radiation brings additional capabilities for the remote sensing, allowing for measurements of internal vibrations of the object due to penetrating capabilities of microwave radiation. The frequency of the microwave radiation can be the same as the modulating frequency of the optical signal, thus allowing for a shared use of electronic circuitry for both received microwave and optical signals.

The present invention also employs an innovative method and algorithm for enhanced performance of the vibrometer by using an additional set of acoustic transmitters/receivers attached directly to the electromagnetic wave transducer assembly. This additional set and corresponding data processing algorithm allow for compensation of the unwanted background, or coupled, vibration of the vibrometer and for calibrated measurements of the displacement of the vibrating object irradiated under an arbitrary angle.

Figure 2:
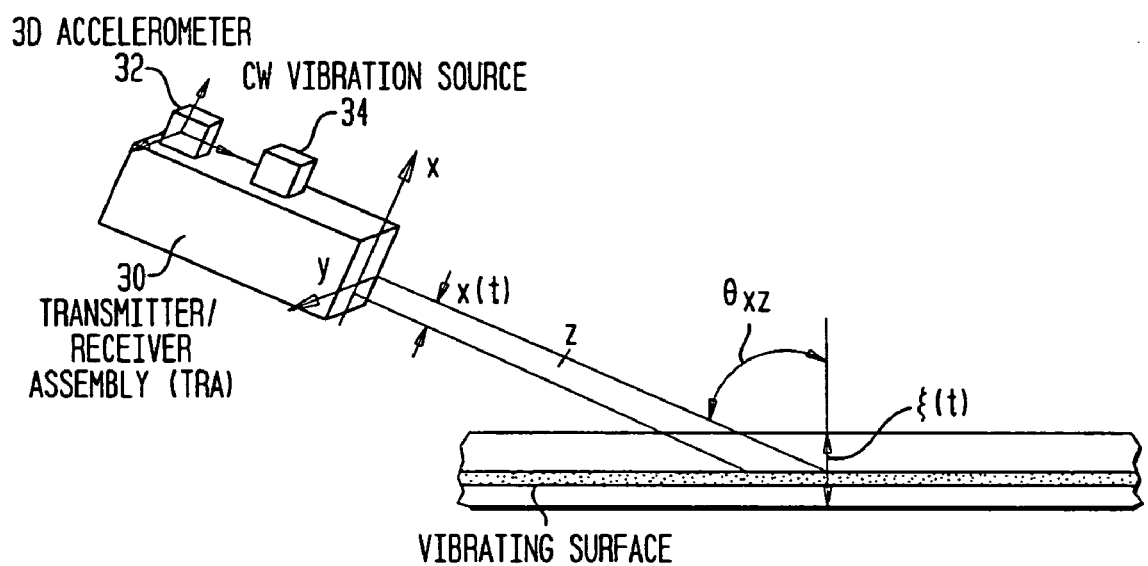
FIG. 2 is a schematic view of the method and apparatus for compensating for errors arising from unwanted vibration of the transmitting/receiving assembly (TRA).

Referring to FIG. 2, the method and algorithm for compensating for cosine and transmitter/receiving assembly (TRA) 30 vibration errors, is shown. A 3D accelerometer 32 (or any motion sensor) and a CW (continuous wave) source 34 of vibration at frequency $f_0$, are attached to the TRA 30. The 3D sensor 32 measures three components of the TRA vibration displacements: x(t), y(t), and z(t). The output of the TRA 30 is proportional to the variation in the length, L(t), between the TRA 30 and the surface of the tested object 8. L(t) can be defined using FIG. 2 geometry. For simplicity only the XZ-plate dependent (2D case) is considered:

$$L(t)=\xi(t)/\cos\Theta_{xz}+x(t)\sin\Theta_{xz}/\cos\Theta_{xz}+z(t) \quad (1)$$

where $\xi(t)$ is the normal displacement of the vibrating object, and $\Theta_{xz}$ is the angle between the normal to the surface of the object 8 and z-axes of the TRA 30. Here x(t) and z(t) are unwanted components of the output signal. The signal z(t) can be easily compensated (subtracted) since it is directly measured with the 3D sensor 32. However to compensate for x(t), the angle $\Theta_{xz}$ must be determined. This can be done using a CW vibration source 34, which causes the TRA 30 to vibrate at a fixed frequency $f_0$ with amplitude $A_{ox}$. Taking this vibration into account, Eq. (1) can be re-written as:

$$L(t)-z(t)=[\xi(t)/\sin\Theta_{xz}+x(t)+A_{ox}\cos(2\pi f_0 t)]\tan\Theta_{xz}. \quad (2)$$

By choosing the applied vibration large enough that $A_{ox} \gg [\xi(t)/\sin\Theta_{xz}+x(t)]$, the output signal at the known frequency $f_0$ can be used to evaluate unknown angle $\Theta_{xz}$:

$$L(t)-z(t)|_{f=f_0} \approx A_{ox}\tan\Theta_{xz}. \quad (3)$$

Thus, formula (3) can be used to evaluate the angle $\Theta_{xz}$ and knowing x(t) and z(t), which are measured with the 3D sensor 32, the true displacement $\xi(t)$ can be determined using formula (1).

This algorithm can be easily extended for the 3D case, in which a vibrating source generates x and y components of vibration and the 3D sensor also measures the y component of the TRA vibration.

The apparatus of the present invention comprises an optical or microwave transmitter, corresponding receiver, and electronics including power supplies, signal generators, amplifiers, modulators, demodulators, acquisition and processing units.

Figure 3A:
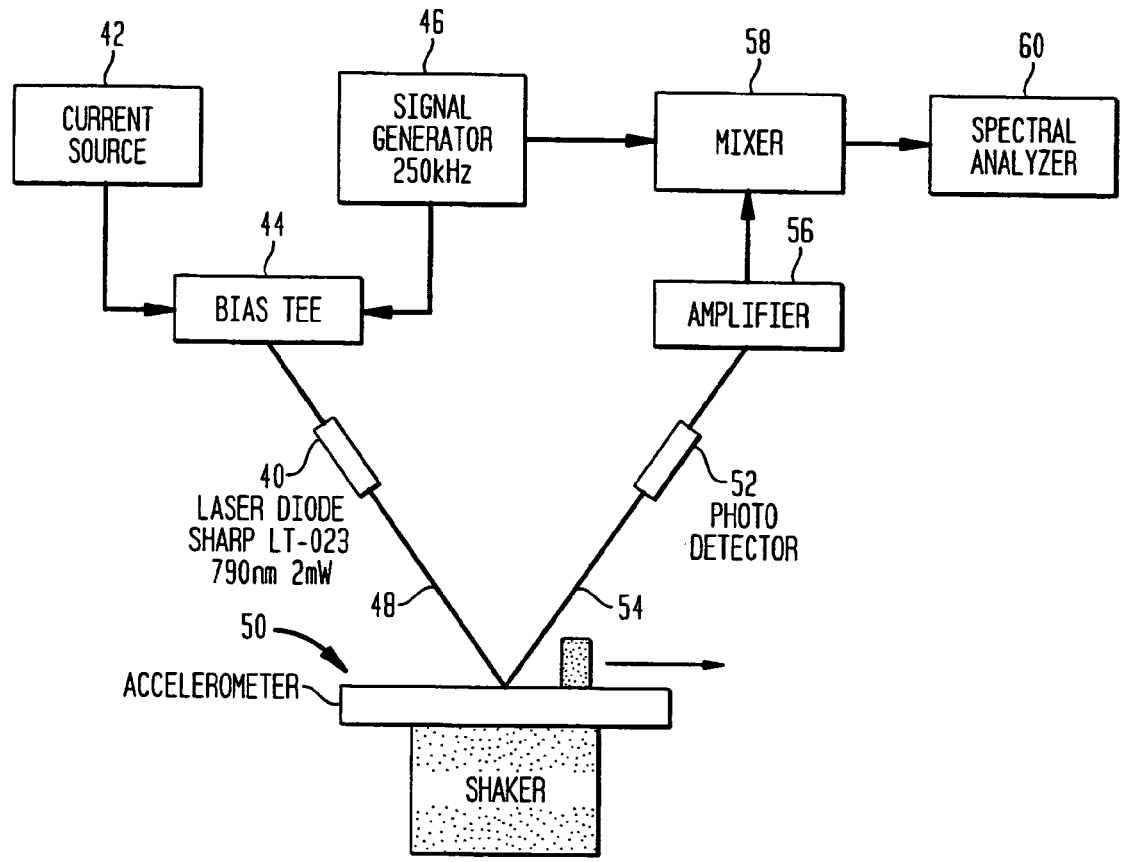
FIG. 3a is a schematic view of an experimental set-up of the method and apparatus of the present invention.

FIG. 3a is a schematic view of an experimental setup of the present invention. A laser diode 40 is used as the source of light. One suitable laser diode is the Sharp LT-023, having a wavelength of 790 nm and 2 mW of power. Any other suitable light source can be used. Coherency of the light source is not too important, and accordingly, even and LED could be used. The laser diode 40 is powered by current source 42 which supplies current to drive the laser 40. The current goes through a bias tee 44 which is an electronic scheme which allows for the modulation of the current supplied to the laser diode 40. The current is modulated by the signal from signal generator 46, at for example 250 kHz. However, for better results in practice, the modulating signal is in the GHz range, i.e. a few GHz or higher, because the device is more sensitive at higher frequencies. The intensity of the laser signal is thereby amplitude modulated.

The modulated signal 48 is then sent at the object 50. The signal 48 is reflected or scattered by the object 50, and the reflected signal 54 is received by photodetector 52. In the experimental setup shown, the vibrating object 50 comprises a shaker and an accelerometer to make actual measurements of the vibration for comparison to experimental results. The reflected signal 54 received by the photodetector 52 is proportional to intensity. The amplitude modulated signal 48 is additionally modulated in phase by the vibration of the object 50 such that reflected signal 54 is amplitude and phase modulated. The reflected signal 54 is then amplified by amplifier 56 and fed to mixer 58 which also receives a signal from the signal generator 46. The mixer 58 mixes these signals, the phase modulated signal and the reference signal to demodulate the reflected signal, which is sent to the spectral analyzer 60.

Figure 3B:
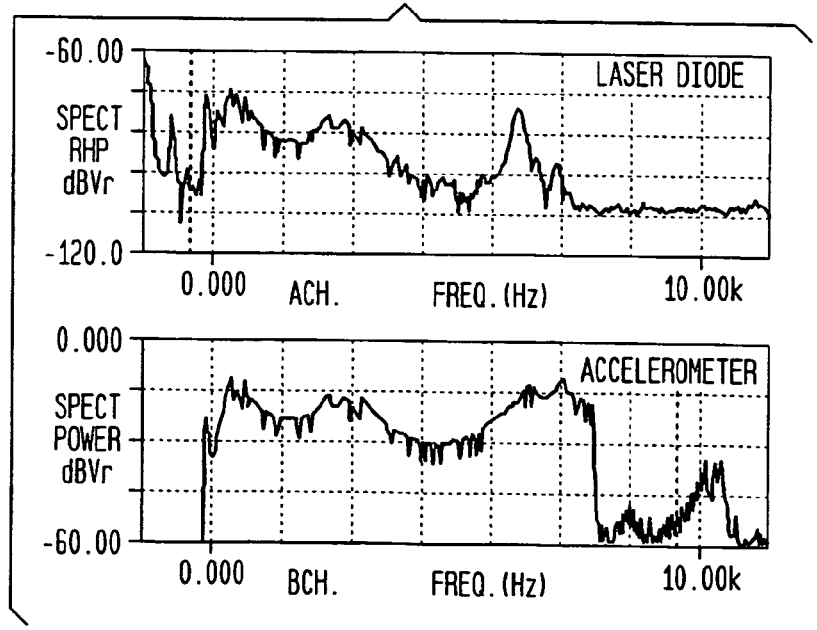

FIG. 3b graphically shows the frequency response of the vibrating object measured by the laser of the present invention and as measured directly by the accelerometer. As can be seen, the present invention measures the vibration in accordance with measurements taken directly of a vibrating object. As the modulating frequency is increased, the results become more accurate.

Figure 4:
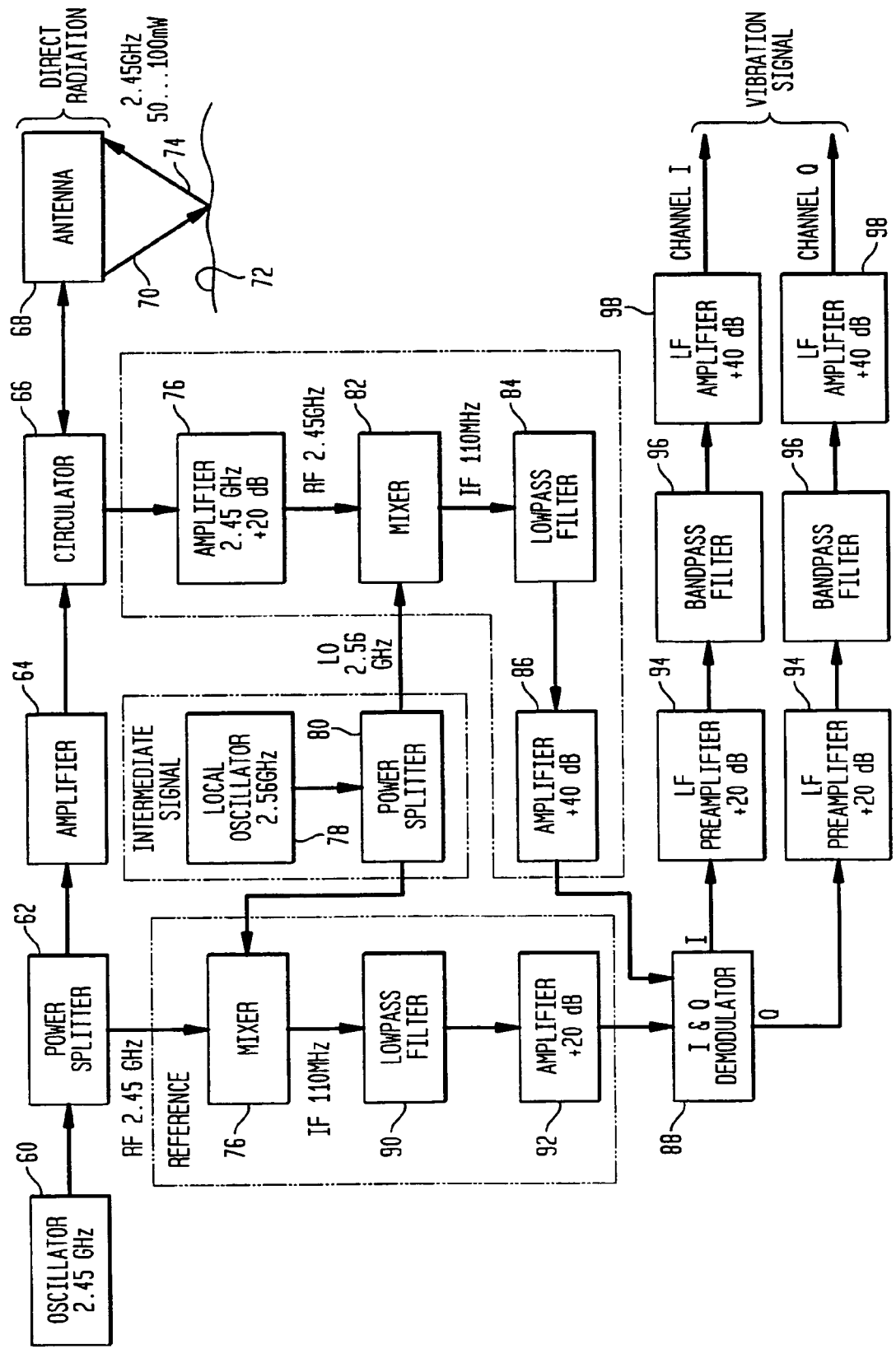
FIG. 4 is a schematic of a microwave vibrometer embodiment of the present invention.

FIG. 4 is a schematic of a microwave vibrometer embodiment of the present invention. An oscillator or signal generator 60 generates a signal at, for example, 2.45 GHz. The signal is split by power splitter 62. Part of the signal goes to mixer 76 where it will later be used. The other part of the signal is sent to amplifier 64 where it is amplified and then to circulator 66 and then to antenna 68 which sends signal 70 to vibrating surface 72 where it is reflected, scattered and modulated. Modulated signal 74 is also received by the antenna 68 and sent back to the circulator 66 which decouples the signal. This signal is then sent to amplifier 76 and then to mixer 82 which is part of a heterodyne scheme including second oscillator 78 which sends a signal at an intermediate frequency, for example 2.56 GHz, through power splitter 80 to mixer 82. In this way, the reference signal and the reflected signal are not mixed directly, but rather each is mixed with an intermediate frequency, which provides advantages in terms of signal to noise ratio. The signal leaving the mixer 82 is the difference of 2.56 GHz and 2.45 GHz which is the intermediate frequency (IF) of 110 MHz. This signal is sent to low pass filter 84 and then to amplifier 86 and then to I&Q demodulator 88. Mixer 76 receives signals from both oscillators 60 and 78 through power splitters 62 and 80 respectively, and sends them to low pass filter 90 and then through amplifier 92 to I&Q demodulator 88. I&Q demodulator 88 functions essentially as a mixer which demodulates the signal into real and imaginary parts which correspond to amplitude and phase. These signals are sent through preamplifiers 94, bandpass filters 96 and amplifiers 98.

The present invention can be used as a remote sensing device used for various applications, including, but not limited to, nondestructive testing, characterization and monitoring of mechanical structures and civil structures (bridges, storage tanks, etc), air- and car-frames, pipes, pressure vessels, weldments, engines, etc.

Accordingly, the present invention provides a method and apparatus that relates to an electromagnetic wave vibrometer which generates an electromagnetic signal and transmits the signal at a vibrating object. A receiver for receiving a reflected or scattered phase modulated signal from the vibrating object is provided and feeds the signal to a demodulator for demodulating the received signal and a signal processor for analyzing the vibration waveform. Additionally, a method and apparatus is provided for remotely measuring properties of an object including a signal generator for generating an electromagnetic signal and transmitting a signal at an object. A means for vibrating the object is provided. The vibrating object phase modulates the transmitted signal. A receiver picks up the reflected and scattered phase modulated signal and a demodulator demodulates the received signal and a signal processor analyzes the vibration waveform. Similarly, the present invention relates to methods for remotely measuring vibration and remotely determining properties of an object.

Having thus described the invention in detail, it is to be understood that the foregoing description is not intended to limit the spirit and scope thereof. What is desired to be protected by Letters Patent is set forth in the appended claims.

What is claimed is:

1. An electromagnetic wave vibrometer apparatus comprising:
    a signal generator for generating an electromagnetic signal;
    an amplitude modulator for amplitude modulating the electromagnetic signal to produce an amplitude modulated signal;
    a first transmitter for transmitting the amplitude modulated signal at a vibrating object;
    a first receiver for receiving a reflected amplitude modulated signal from the vibrating object;
    a second vibration receiver mounted with the first receiver for compensation of unwanted background or coupled vibration;
    a demodulator for demodulating the reflected amplitude modulated signal to produce a demodulated signal; and
    a signal processor for extracting and analyzing a vibration waveform from the demodulated signal.

2. The apparatus of claim 1 wherein the electromagnetic signal is an optical signal.

3. The apparatus of claim 2 wherein the optical signal is amplitude modulated with a microwave frequency signal.

4. The apparatus of claim 1 wherein the electromagnetic signal is a microwave signal.

5. The apparatus of claim 1 wherein the electromagnetic signal is a combination of optical and microwave signals.

6. The apparatus of claim 5 wherein the optical and microwave signals are modulated at the same frequency.

7. The apparatus of claim 1 further comprising a laser signal source.

8. The apparatus of claim 1 further comprising an LED signal source.

9. The apparatus of claim 1 further comprising a second vibration transmitter mounted with the first receiver for calibration of the apparatus and to determine an angle of reflection.

10. An apparatus for remotely measuring properties of an object comprising:
    a signal generator for generating an electromagnetic signal;
    an amplitude modulator for amplitude modulating the electromagnetic signal with a modulating signal to produce an amplitude modulated signal;
    a transmitter for transmitting the amplitude modulated signal at an object;
    means for vibrating the object to modulate the amplitude modulated signal transmitted at the object;
    a first receiver for receiving a reflected amplitude modulated signal from the object;
    a second vibration receiver mounted with the first receiver for compensation for unwanted background or coupled vibration;
    a demodulator for demodulating the reflected amplitude modulated signal using the modulating signal to produce a demodulated signal; and
    a signal processor for extracting and analyzing a vibration waveform from the demodulated signal.

11. The apparatus of claim 10 wherein the electromagnetic signal is an optical signal.

12. The apparatus of claim 11 wherein the optical signal is amplitude modulated with a microwave frequency signal.

13. The apparatus of claim 10 wherein the electromagnetic signal is a microwave signal.

14. The apparatus of claim 10 wherein the electromagnetic signal is a combination of optical and microwave signals.

15. The apparatus of claim 14 wherein the optical and microwave signals are modulated at the same frequency.

16. The apparatus of claim 10 further comprising a laser signal source.

17. The apparatus of claim 10 further comprising an LED signal source.

18. The apparatus of claim 10 further comprising a second vibration transmitter mounted with the first receiver for calibration of the apparatus and to determine an angle of reflection.

19. The method of claim 10, wherein the amplitude modulated signal is modulated in the GHz range.

20. A method of remotely measuring vibration comprising:
    generating an electromagnetic signal;
    amplitude modulating the electromagnetic signal with an amplitude modulating signal to produce an amplitude modulated signal;
    transmitting the amplitude modulated signal at a vibrating object using a first transmitter;
    receiving a reflected amplitude modulated signal from the vibrating object using a first receiver;
    demodulating the reflected amplitude modulated signal using the amplitude modulating signal to produce a demodulated signal;

compensating for vibration errors by determining displacements of the transmitter and receiver; and
analyzing the demodulated signal.

21. The method of claim 20 wherein the electromagnetic signal is an optical signal.

22. The method of claim 20 wherein the electromagnetic signal comprises a microwave signal.

23. The method of claim 20 wherein the electromagnetic signal comprises a combination of microwave and optical signals.

24. The method of claim 23 wherein the optical and microwave signals are modulated at the same frequency.

25. The method of claim 20 wherein the electromagnetic signal is generated by a laser or a laser diode.

26. The method of claim 20 wherein the electromagnetic signal is generated by an LED.

27. The method of claim 20 further comprising providing a second vibration receiver mounted with the first receiver for compensating for unwanted background or coupled vibration.

28. The method of claim 27 further comprising providing a second vibration transmitter mounted with the first receiver for calibrating the vibrometer and to determine an angle of reflection.

29. The method of claim 20, wherein the amplitude modulated signal is modulated in the GHz range.

30. A method for remotely determining properties of an object comprising:
amplitude modulating an electromagnetic signal with an amplitude modulating signal to produce an amplitude modulated signal;
transmitting the amplitude modulated signal at an object;
vibrating the object;
receiving reflected amplitude modulated signals from the vibrating object using a first receiver;
compensating for unwanted vibration using a second receiver mounted with the first receiver; and
processing the reflected amplitude modulated signals to extract information about the properties of the object.

31. The method of claim 30 wherein the electromagnetic signal is an optical signal.

32. The method of claim 30 wherein the electromagnetic signal comprises a microwave signal.

33. The method of claim 30 wherein the electromagnetic signal comprises a combination of microwave and optical signals.

34. The apparatus of claim 30 wherein the optical and microwave signals are modulated at the same frequency.

35. The method of claim 30 wherein the electromagnetic signal is generated by a laser or a laser diode.

36. The method of claim 30 wherein the electromagnetic signal is generated by an LED.

37. The method of claim 30 wherein the electromagnetic signal is split into first and second signals and the second signal is transmitted to a demodulator for comparing the second signal with the reflected amplitude modulated signals.

38. The method of claim 30 further comprising providing a second vibration transmitter mounted with the first receiver for calibrating the vibrometer and to determine an angle of reflection.

39. The method of claim 1, wherein the amplitude modulated signal is modulated in the GHz range.

40. The method of claim 30, wherein the amplitude modulated signal is modulated in the GHz range.

41. A method of remotely measuring vibration, comprising:
providing a non-coherent beam of light;
amplitude modulating the non-coherent beam of light with an amplitude modulating signal to produce an amplitude modulated beam of light;
transmitting the amplitude modulated beam of light at a vibrating object; object using a transmitter;
receiving a reflected amplitude modulated beam of light from the vibrating object using a receiver;
compensating for vibration errors by determining displacements of the transmitter and the receiver; and
demodulating the reflected amplitude modulated beam of light using the amplitude modulating signal to extract vibration information from the amplitude modulated signal.

42. The method of claim 41, wherein the non-coherent beam of light is produced by an LED.

43. The method of claim 41, wherein the non-coherent beam of light is an optical signal.

44. The method of claim 41, further comprising compensating for unwanted background or coupled vibration using a second receiver.

45. The method of claim 44, further comprising determining an angle of reflection using a second vibration transmitter mounted with the receiver.

46. A microwave vibrometer, comprising:
a signal generator for generating a first microwave frequency signal;
a power splitter for splitting the first microwave signal into a reference signal and a signal to be transmitted;
a circulator for transmitting the signal to be transmitted at a vibrating object, for receiving a phase modulated reflected signal from the vibrating object, and for decoupling the transmitted signal from the reflected signal;
a first mixer for mixing the phase modulated reflected signal with an intermediate frequency signal to produce a first mixed signal;
a second mixer for mixing the reference signal with the intermediate frequency signal to produce a second mixed signal;
an I & Q demodulator for mixing the first mixed signal and the second mixed signal to produce a demodulated signal; and
means for extracting and analyzing a vibration waveform from the demodulated signal.

* * * * *